(12) United States Patent
Tanaami et al.

(10) Patent No.: US 6,919,201 B2
(45) Date of Patent: Jul. 19, 2005

(54) BIOCHIP MEASURING METHOD AND MEASURING EQUIPMENT

(75) Inventors: Takeo Tanaami, Musashino (JP); Yumiko Sugiyama, Musashino (JP)

(73) Assignee: Yokogawa Electric Corporation, Tokyo (JP)

(*) Notice: Subject to any disclaimer, the term of this patent is extended or adjusted under 35 U.S.C. 154(b) by 7 days.

(21) Appl. No.: 10/728,810

(22) Filed: Dec. 8, 2003

(65) Prior Publication Data

US 2004/0115797 A1 Jun. 17, 2004

(30) Foreign Application Priority Data

Dec. 11, 2002 (JP) .................................. 2002-359033

(51) Int. Cl.[7] .............................................. C12M 1/36
(52) U.S. Cl. .......................... 435/286.2; 435/287.3; 435/288.4; 435/288.7; 356/409; 356/425; 382/128; 382/254; 382/274
(58) Field of Search .................... 435/286.2, 287.3, 435/288.4, 288.7; 356/409, 425; 382/128, 254, 274

(56) References Cited

U.S. PATENT DOCUMENTS 5,686,960 A * 11/1997 Sussman et al. ........ 348/218.1
2004/0253614 A1 * 12/2004 Yonekawa et al. ............ 435/6

FOREIGN PATENT DOCUMENTS

| JP | 2002-207007 | | 7/2002 |
| WO | WO99/05574 | * | 2/1999 |

* cited by examiner

Primary Examiner—David Redding
(74) Attorney, Agent, or Firm—Westerman, Hattori, Daniels & Adrian, LLP

(57) ABSTRACT

When a plurality of types of biopolymers on a biochip is to be measured using a fluorescence or colorimetric means, the image of the above biochip is obtained by measuring a plurality of images while moving the above biochip stepwise by an integer multiple of the field-of-view of a one-dimensional or two-dimensional array detector on the sample, then by combining the above-described plurality of images.

6 Claims, 4 Drawing Sheets

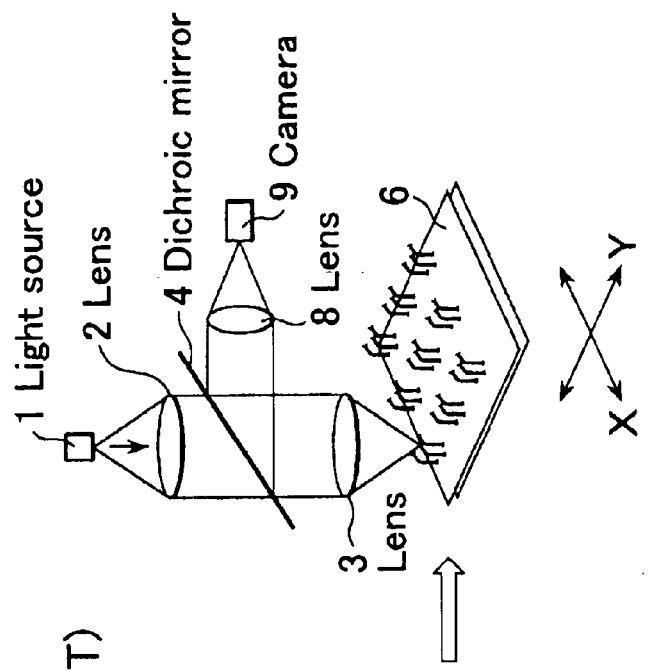
FIG.1C (PRIOR ART)
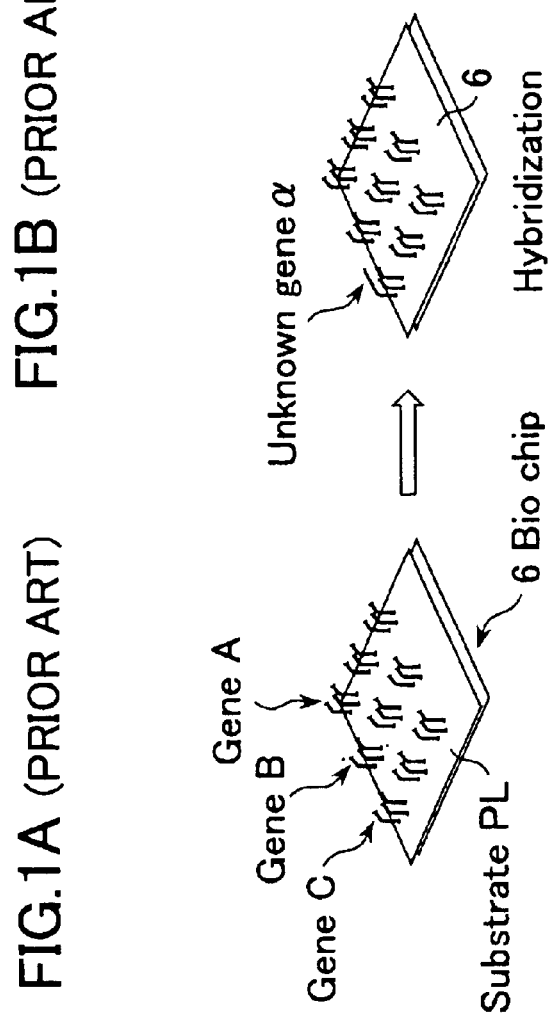
FIG.1B (PRIOR ART)
FIG.1A (PRIOR ART)

10 Mesurment area
11
11
Non-sample area

31 Line camera
Movement
6 Sample

BIOCHIP MEASURING METHOD AND MEASURING EQUIPMENT

BACKGROUND OF THE INVENTION

1. Field of the Invention

The present invention relates to a biochip reader for measuring a plurality of types of biopolymers on a substrate, and in particular, relates to an improvement for enabling the measurement of a wider area on a substrate while maintaining a large numerical aperture.

2. Description of the Prior Art

There is well-known equipment which detects and analyze DNA or protein by labeling biopolymers such as DNA or protein with fluorescent materials, exciting those fluorescent materials through irradiation of the biopolymers with laser, and reading the fluorescence generated from the fluorescent materials. In this case, biochips on which DNA or protein or the like labeled with fluorescent materials is spotted in an array are utilized.

FIG. 1 is a conceptual configuration drawing showing an example of conventional incident-light fluorescence biochip readers mentioned in the gazette of Japanese Laid-open Patent Application No. 2000-207007. This biochip reader reads hybridization of unknown gene α as shown in FIG. 1(b) and biochip 6 composed of a plurality of DNA molecules (genes) A, B, C, . . . whose sequences are known bonded on substrate PL as shown in FIG. 1(a) using a mechanism as shown in FIG. 1(c).

In FIG. 1(c), light from light source 1 (laser) becomes the parallel light at lens 2 and, after transmitting dichroic mirror 4, is focused on biochip (or called a sample) 6 by means of lens 3. The light returned from biochip 6 becomes parallel again by means of lens 3 and is reflected with dichroic mirror 4 and forms an image on camera 9 by means of lens 8.

In this case, the surface of biochip 6 is scanned by moving the stage (not shown in the drawing) on which biochip 6 is mounted in the directions of X and Y using a driving means (not shown in the drawing) to obtain the image of the surface of biochip 6.

However, there are the following problems with such conventional systems:

(1) FIG. 2 is a drawing for the optical system shown in FIG. 1. The measurable range is determined by the CCD camera used and magnifications of lenses 3 and 8 and the following relations exist between them:

$$a_1/a_2 = f_1/f_2 = NA_2/NA_1$$

where $a_1$ is the width of measurement area (field of view of camera 9) of biochip 6.
$a_2$ is the width of the detecting element surface of camera 9.
$f_1$ is the focal length of lens 3.
$f_2$ is the focal length of lens 8.
$NA_1$ is the numerical aperture of lens 3.
$NA_2$ is the numerical aperture of lens 8.

Due to these relations, if measurement area $a_1$ is widened, the image becomes dark because the incident $NA_1$ becomes small.

(2) When the size of the detecting element, CCD, of camera 9 is, for example, ½ inch, its field of view is about 4.8×6.4 mm². This value is about 1/60 smaller than the measurement area of 75×25 mm² in the case where sample 6 is, for example, a slide glass. Furthermore, in the case of the system where conventional one-beam laser irradiates a sample which is moved with a stage, and the total light quantity for each step is detected with photomultipliers or the like, a precision stage is required and so the system is expensive and measurement is time-consuming. If it is assumed that measurement is made in about 10-μm step using one-beam exciting light, a measurement area of 75×25 mm² must be measured by moving the stage $1.875×10^7$ times.

SUMMARY OF THE INVENTION

The present invention is intended to solve the above-described problems; the objective is to achieve a measuring method and measuring equipment for biochips that can measure images in bright conditions over a wide biochip measurement area.

BRIEF DESCRIPTION OF THE DRAWINGS

[FIG. 1]

FIG. 1 is a conceptual configuration drawing showing an example of conventional incident-light fluorescence biochip readers.

FIG. 2 is a drawing illustrating the relationships in the optical system of the above example.

FIG. 3 is a principle diagram describing the principle of the biochip measuring method of the present invention.

FIG. 4 is a drawing illustrating jumped movement.

FIG. 5 is a drawing indicating the configuration of the essential part in the case of using a line camera of one-dimensional array.

FIG. 6 is a drawing showing another embodiment of step movement.

FIG. 7 is a drawing illustrating the position where images of the field-of-view images are joined.

DETAILED DESCRIPTION OF THE PREFERRED EMBODIMENTS

The biochip measuring method or measuring equipment of the present invention is a measuring method or measuring equipment which measures a plurality of types of biopolymers on a substrate using fluorescence or calorimetric means. The present invention will be described below in detail using the drawings.

Figure 2:
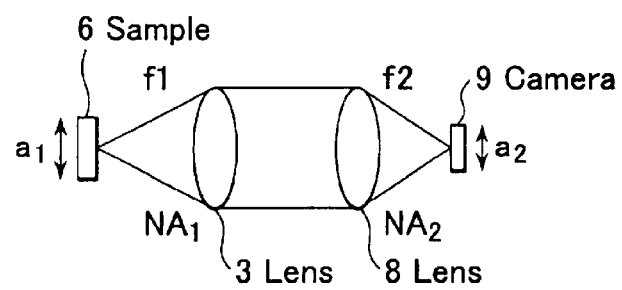
[FIG. 2]
Figure 3:
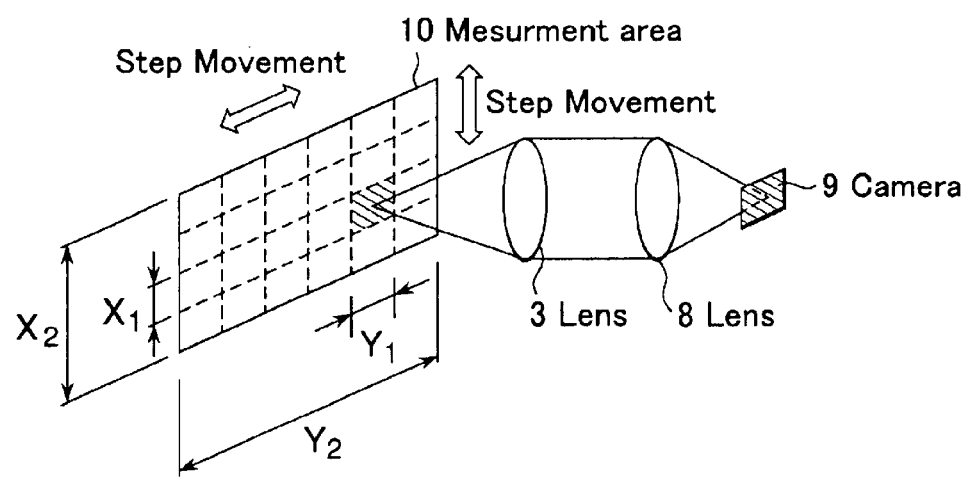
[FIG. 3]

FIG. 3 is a principle diagram describing the principle of the biochip measuring method of the present invention. In FIG. 3, the items equivalent to those shown in FIG. 1 are given the same signs. If measurement area $(X_2, Y_2)$ 10 of sample 6 is wider than the field of view $(X_1, Y_1)$ of camera 9, a plurality of images is photographed with camera 9 over the whole measurement area by moving sample 6 step-wise by an integer multiple of the above field of view using a stage (not shown in the drawing). Then, the entire image is made by combining that plurality of images (called the field-of-view images) using an image processing means (not shown in the drawing).

For example, if $X_2$ and $Y_2$ of measurement area $(X_2, Y_2)$ 10 are 75 mm and 25 mm respectively, the relationships between the CCD size (and the size of the field of view in that case) and the number of times of step-wise movement are as shown in the table below.

TABLE 1

| CCD | Field of View | Number of Times of Movement |
| --- | --- | --- |
| ½ inch | X1 = 6.4 mm | X direction: 12 times |
| | Y1 = 4.8 mm | Y direction: 6 times |
| ⅓ inch | X1 = 4.8 mm | X direction: 16 times |
| | Y1 = 3.6 mm | Y direction: 7 times |
| ⅕ inch | X1 = 2.95 mm | X direction: 26 times |
| | Y1 = 2.21 mm | Y direction: 12 times |

In this case, border parts of images adjacent to each other are first measured in an overlapped manner and then, if there are shifts, those positions are corrected within the image plane. In addition, if there is unevenness of light quantity in the image plane, the unevenness is corrected. These corrections are implemented in the image processing means.

Furthermore, the present invention is not restricted to the above embodiment but may be embodied in other specific forms, changes, and versions without departing from the spirit or essential characteristics thereof.

For instance, for the above described stage moving mechanism, mechanisms which are moved using an electromagnetic drive, electrostatic drive, piezo-electric drive, or the like, can be used.

Figure 4:
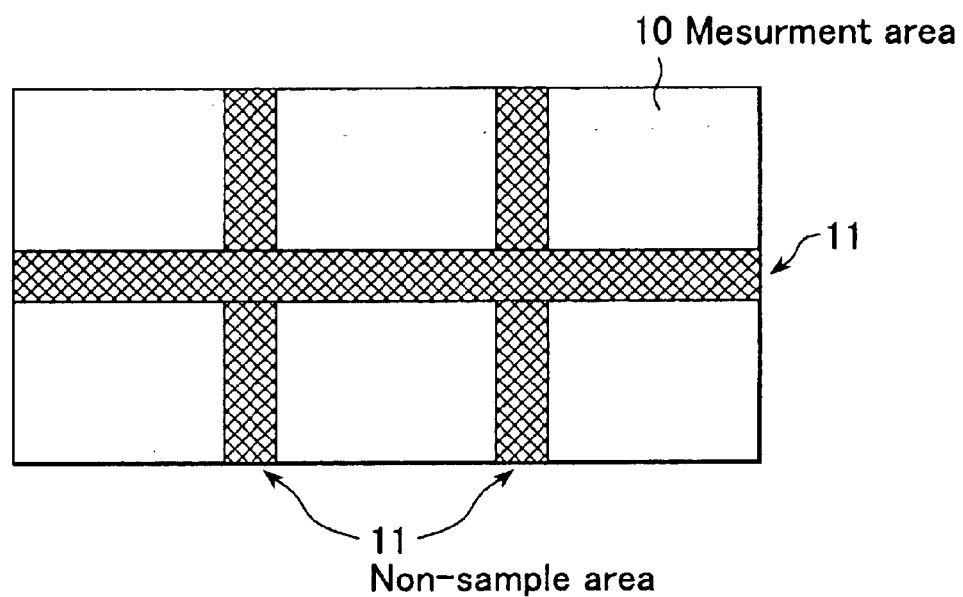
[FIG. 4]

In image measurement, step movement involving jumping over non-sample areas 11 in measurement area 10 (that is, jumping movement) as shown in FIG. 4 may be employed.

Figure 5:
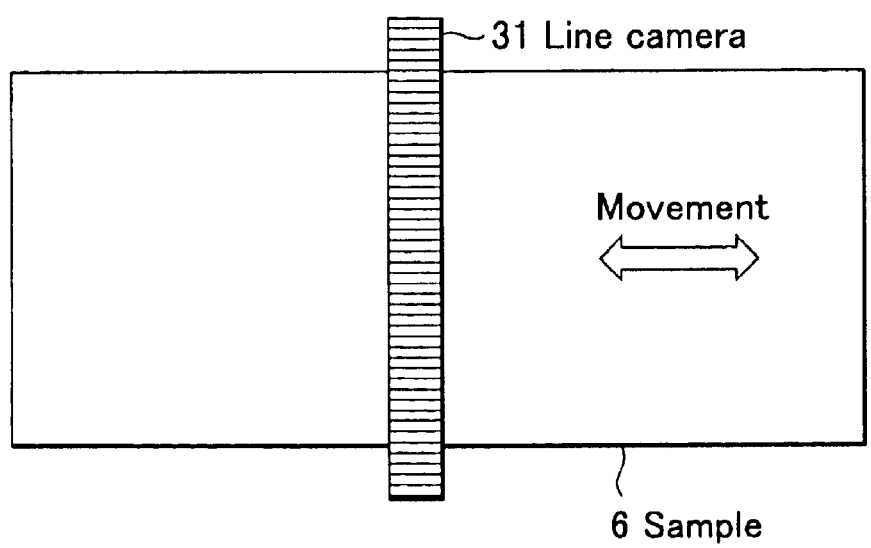
[FIG. 5]

Further, as shown in FIG. 5, measurement may be made by moving sample 6 step-wise in the direction orthogonal to the camera array direction by means of single-shaft driving, using line camera 31 in which detector elements are arrayed one-dimensionally as a camera to be employed.

Figure 6:
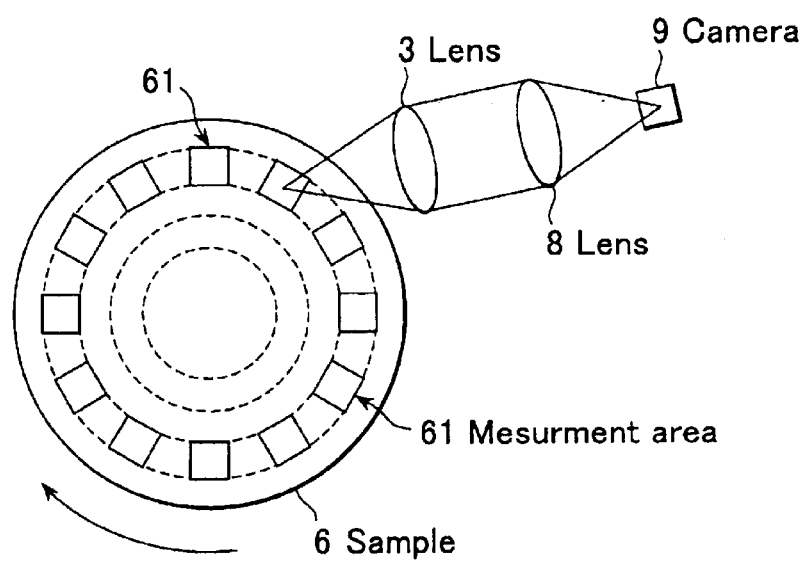
[FIG. 6]

Movement relative to the field of view on sample 6 is not restricted to the movement in the orthogonal direction as in the embodiment described above but may be rotational movement such as ringed or helical as shown in FIG. 6. In this case, each measurement area 61 should also be arranged ringed or helically.

Further, for step movement, the prescribed measurement area can be covered within 50 steps on each axis of Cartesian coordinates or polar coordinates.

Figure 7A:
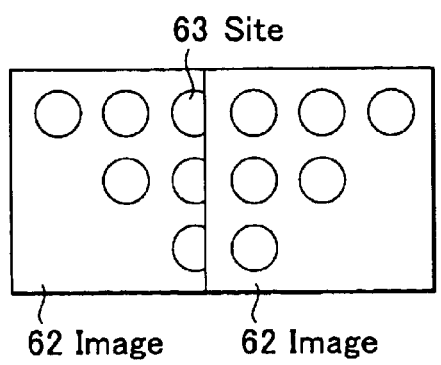
[FIG. 7]
Figure 7B:
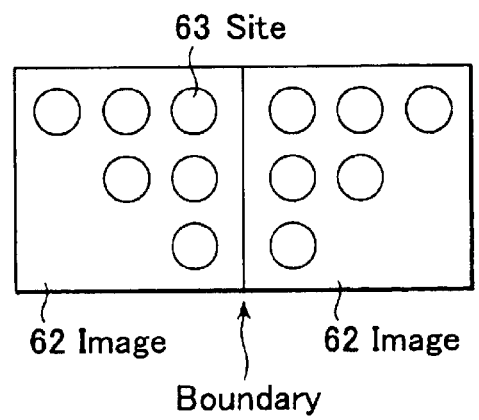

In addition, when images are to be combined, the combination is not made so that adjacent images are overlapped on an image of site 63 in field-of-view image 62 as shown in FIG. 7(a) but it is made at the end (boundary) of field-of-view image 62. In other words, the combination of images can be facilitated by ingeniously utilizing the fact that there are gaps between sites (DNA spots).

As described above, the present invention has the following effects:

(1) Biochips must be measured at high sensitivity because of trace amounts of expressed genes or the like. This requires a large numerical aperture (NA). According to the present invention, images can be easily measured over a wide area while maintaining the large NA.

(2) In measuring the entire measurement area, a far smaller number of movements is required than in conventional stage scans. Accordingly, it is sufficient for the purpose of measurement to employ simpler, cheaper moving mechanisms.

What is claimed is:

1. A biochip measuring method for measuring a plurality of types of biopolymers on a biochip using fluorescence or colorimetric means, comprising measuring a plurality of images, moving said biochip step-wise by an integer multiple of the field of view on the sample of a one- or two-dimensional array detector, then obtaining an image of said biochip by combining said plurality of images.

2. A biochip measuring method in accordance with claim 1, wherein the number of said moving steps is within 50 on each axis of Cartesian coordinates or polar coordinates on the plane of said biochip.

3. A biochip measuring method in accordance with claim 1 or claim 2, wherein said movement is made by driving a stage on which the sample is mounted using electromagnetic, electrostatic, or piezoelectric means.

4. A biochip measuring method in accordance with claim 1 or claim 2, wherein when the field-of-view images are to be combined in said image combination, said combination is implemented so that the boundary of combination does not overlap with the site part of said biochip.

5. A biochip measuring method in accordance with claim 1 or claim 2, wherein, in measurement of said plurality of images, the images are measured by moving the field-of-view step-wise while jumping over non-sample areas.

6. Biochip measuring equipment for measuring a plurality of types of biopolymers on a biochip using fluorescence or colorimetric means, in which the following items are comprised and a biochip image is obtained by using these items:

a one-dimensional or two-dimensional array detector for measuring images of biopolymers on the surface of said biochip, a stage on which a sample having a measurement area wider than the field-of-view of said array detector is mounted, a driving means that moves said stage step-wise by an integer multiple of the field-of-view of said array detector, and an image combining means which combines a plurality of images of the biochip obtained by said array detector.

* * * * *